(12) United States Patent
Xiao et al.

(10) Patent No.: US 6,960,203 B2
(45) Date of Patent: Nov. 1, 2005

(54) THERMAL ABLATION WITH DEPLOYABLE CAGE

(75) Inventors: Jia Hua Xiao, Bridgewater, NJ (US); Carrie M. Brookner, Bridgewater, NJ (US); Craig Hidalgo, Langhorne, PA (US)

(73) Assignee: Ethicon, Inc., Somerville, NJ (US)

( * ) Notice: Subject to any disclaimer, the term of this patent is extended or adjusted under 35 U.S.C. 154(b) by 158 days.

(21) Appl. No.: 10/183,600

(22) Filed: Jun. 26, 2002

(65) Prior Publication Data

US 2004/0002698 A1 Jan. 1, 2004

(51) Int. Cl.$^7$ ............................................... A61B 18/18
(52) U.S. Cl. .......................................... 606/27; 128/898
(58) Field of Search ........................ 606/27–52, 20–26, 606/41; 128/898; 604/113; 607/122

(56) References Cited

U.S. PATENT DOCUMENTS

| | | | |
|---|---|---|---|
| 3,924,628 A | 12/1975 | Droegemueller et al. | |
| 4,016,867 A | 4/1977 | King et al. | |
| 4,121,572 A | 10/1978 | Krzeminski | |
| 4,204,548 A | 5/1980 | Kurz | |
| 4,685,474 A | 8/1987 | Kurz et al. | |
| 4,764,845 A | 8/1988 | Artus | |
| 4,873,986 A | 10/1989 | Wallace | |
| 4,949,718 A | 8/1990 | Neuwirth et al. | |
| 5,242,390 A | 9/1993 | Goldrath | |
| 5,275,595 A | 1/1994 | Dobak, III | |
| 5,437,629 A | 8/1995 | Goldrath | |
| 5,500,012 A | 3/1996 | Brucker et al. | |
| 5,520,682 A | 5/1996 | Baust et al. | |
| 5,540,658 A | * 7/1996 | Evans et al. | 604/101.04 |
| 5,542,928 A | * 8/1996 | Evans et al. | 604/113 |
| 5,647,868 A | 7/1997 | Chinn | |
| 5,702,438 A | 12/1997 | Avitall | |
| 5,782,899 A | 7/1998 | Imran | |
| 5,800,493 A | 9/1998 | Stevens et al. | |
| 5,868,735 A | 2/1999 | Lafontaine | |
| 5,891,134 A | 4/1999 | Goble et al. | |
| 5,954,714 A | 9/1999 | Saadat et al. | |
| 6,009,877 A | 1/2000 | Edwards | |
| 6,033,397 A | * 3/2000 | Laufer et al. | 606/27 |
| 6,033,398 A | * 3/2000 | Farley et al. | 606/27 |
| 6,139,538 A | * 10/2000 | Houghton et al. | 604/515 |

* cited by examiner

*Primary Examiner*—Michael Peffley
*Assistant Examiner*—Pete Vrettakos

(57) ABSTRACT

A medical device is provided and includes a thermal ablation catheter and a deployable cage assembly for use in thermal ablation therapy. The deployable cage assembly includes a plurality of arms, each of which has a pair of opposed ends attached to the thermal ablation catheter. Each of the arms is movable from a relaxed configuration to a deployed configuration. When relaxed, the arms are substantially proximate to the thermal ablation catheter. When deployed, the arms cooperate with each other to form an open structure which extends radially outward from the thermal ablation catheter. The thermal ablation device also includes a distensible bladder that serves as an endocervical seal.

14 Claims, 9 Drawing Sheets

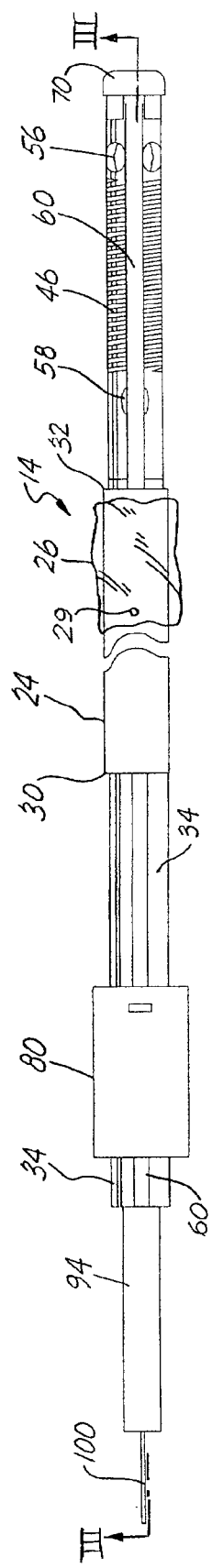
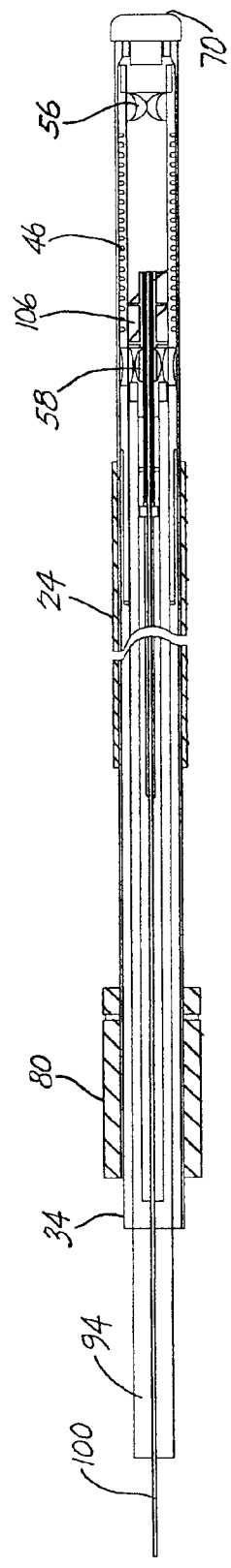
FIG. 2
FIG. 3

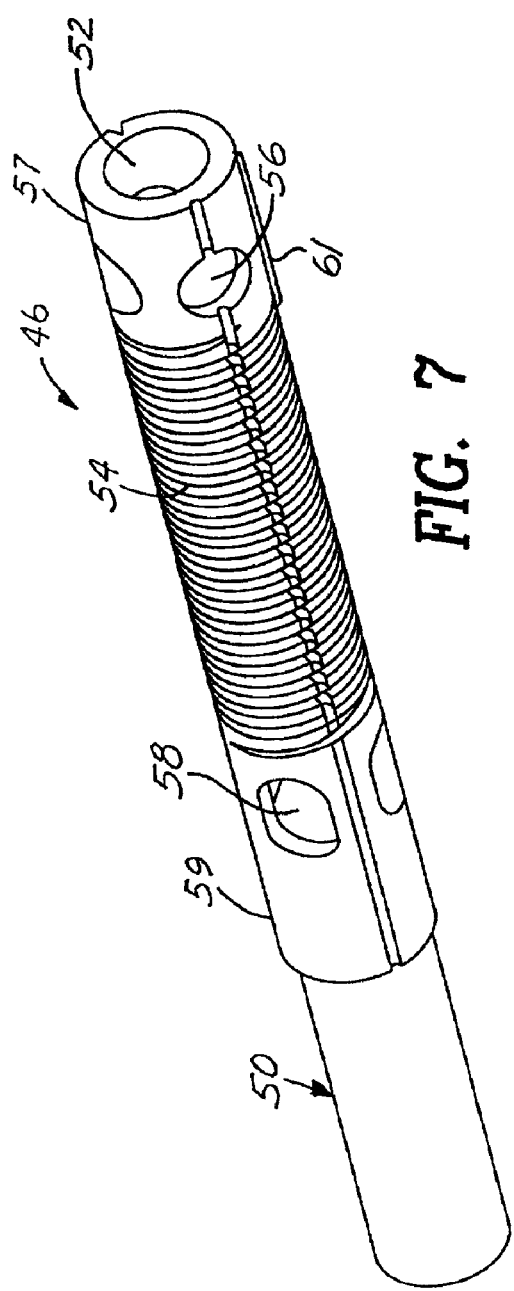
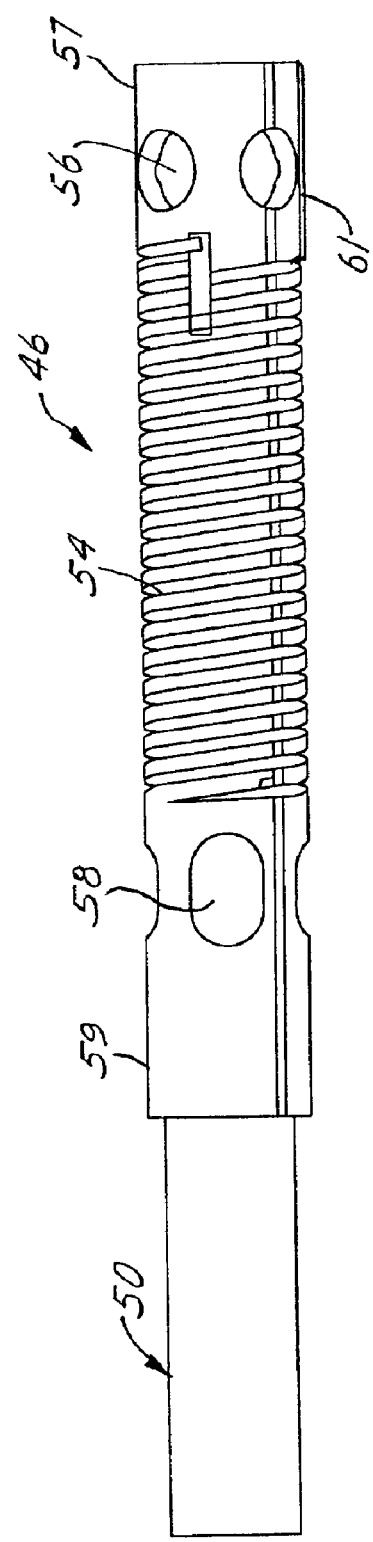
FIG. 7
FIG. 8

THERMAL ABLATION WITH DEPLOYABLE CAGE

FIELD OF THE INVENTION

The present invention relates to a medical device and to a method for thermal ablation, and more specifically to a thermal ablation catheter, having a deployable cage suitable for use in a uterus, for ablation of endometrial cells and tissue within the uterus. As used herein, the term "medical device" includes a medical or surgical device.

BACKGROUND OF THE INVENTION

Millions of women suffer from excessive menstrual bleeding (menorrhagia). A commonly used therapy to treat menorrhagia involves inserting a balloon catheter or a distensible bladder into the uterus, filling the balloon with a thermally conductive fluid, and then heating the fluid to thermally ablate the endometrial lining of the uterus. Although thermal balloon therapy is effective for treating menorrhagia in women who have a smooth uterine lining, such balloon therapy is not recommended for women who have uterine conditions such as myomas, polyps, or irregular uterine shapes, etc.

Accordingly, there is a need for a therapy that involves the use of thermal ablation for treating menorrhagia in women who have benign uterine pathology.

SUMMARY OF THE INVENTION

In accordance with the present invention, there is provided a medical device for use in thermal ablation therapy. The medical device includes a thermal ablation catheter and a deployable cage assembly having a plurality of arms. Each of the arms includes a pair of opposed ends attached to the thermal ablation catheter. Further, each of the arms is movable between a relaxed configuration and a deployed configuration. More particularly, in its relaxed configuration, each of the arms is substantially proximate to the thermal ablation catheter, while in its deployed configuration, it cooperates with the other arms to form an open structure which extends radially outward from the thermal ablation catheter.

In one embodiment, the thermal ablation catheter includes a fluid stem and a plurality of fluid ports in communication with the fluid stem. The fluid ports are surrounded by the open structure.

In accordance with another embodiment, the thermal ablation catheter includes a distensible bladder that serves as an endocervical seal. The distensible bladder is sized and shaped to be inflatable from a collapsed configuration to an expanded configuration.

A method is also disclosed for performing thermal ablation therapy using the medical device. Initially, the distal end of the thermal ablation catheter is inserted into a uterus. The cage assembly is deployed such that it forms an open structure which extends radially outward from the thermal ablation catheter. Then, a fluid is supplied to the uterus through the distal end of the thermal ablation catheter. Lastly, the fluid is conductively heated to a desired temperature which is maintained for a desired time period.

Other features and aspects of the present invention will become more fully apparent from the following detailed description of the exemplary embodiment, the appended claims and the accompanying drawings.

BRIEF DESCRIPTION OF THE DRAWINGS

For a more complete understanding of the present invention, reference is made to the following detailed description of the exemplary embodiment considered in conjunction with the accompanying drawings, in which:

FIG. 2 is a front view of a thermal ablation catheter of the medical device shown in FIG. 1, which shows a deployable cage assembly in a relaxed configuration and a distensible bladder in a collapsed configuration;

FIG. 3 is a cross-sectional view of the thermal ablation catheter shown in FIG. 2, taken along section lines III—III and looking in the direction of the arrows, illustrated without the distensible bladder;

FIG. 7 is a perspective view of a heating assembly;

FIG. 8 is a front view of the heating assembly shown in FIG. 7;

DETAILED DESCRIPTION OF THE EXEMPLARY EMBODIMENT

Figure 1:
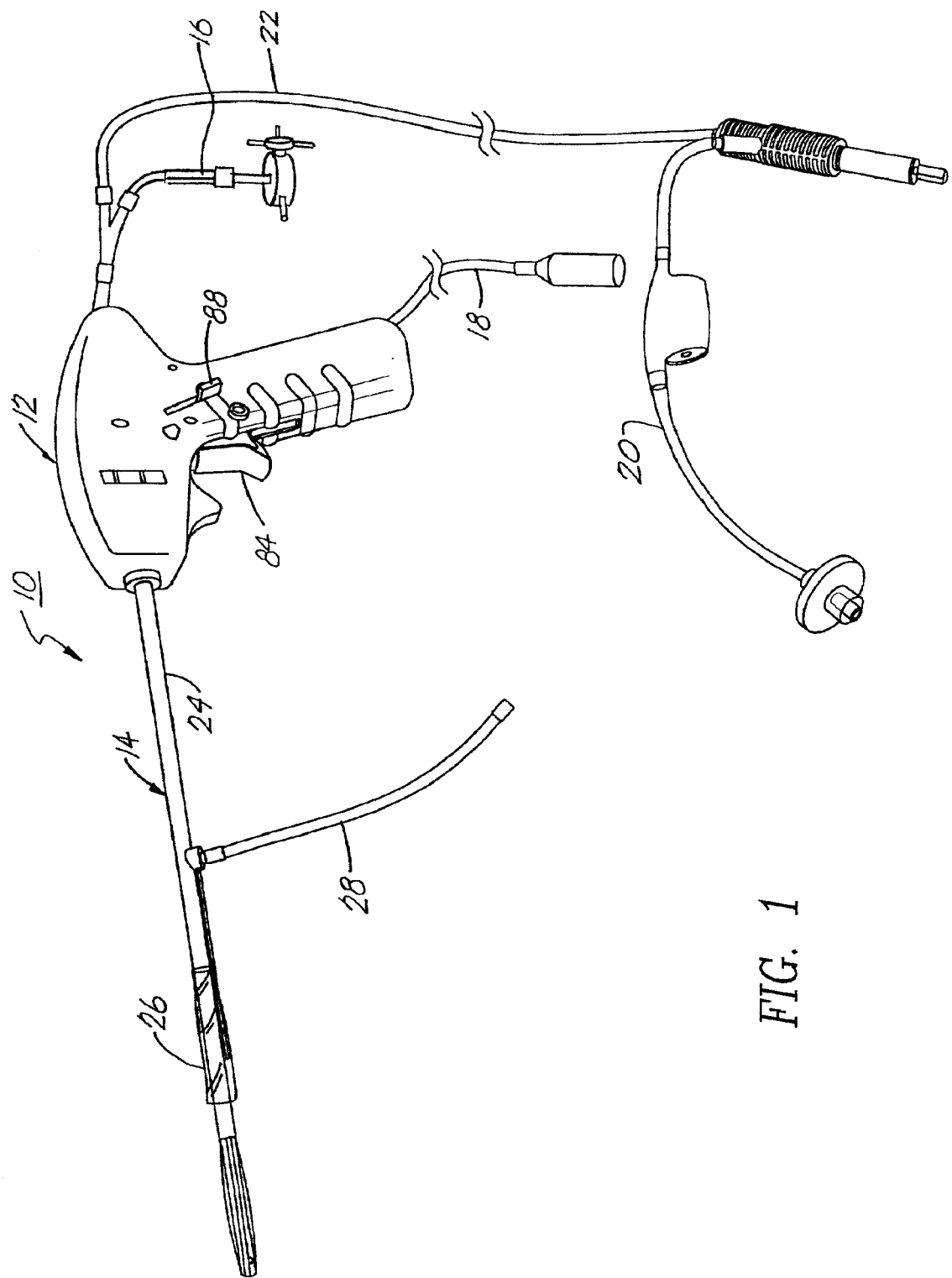
FIG. 1 is a front perspective view of a medical device constructed in accordance with the present invention.
Figure 4:
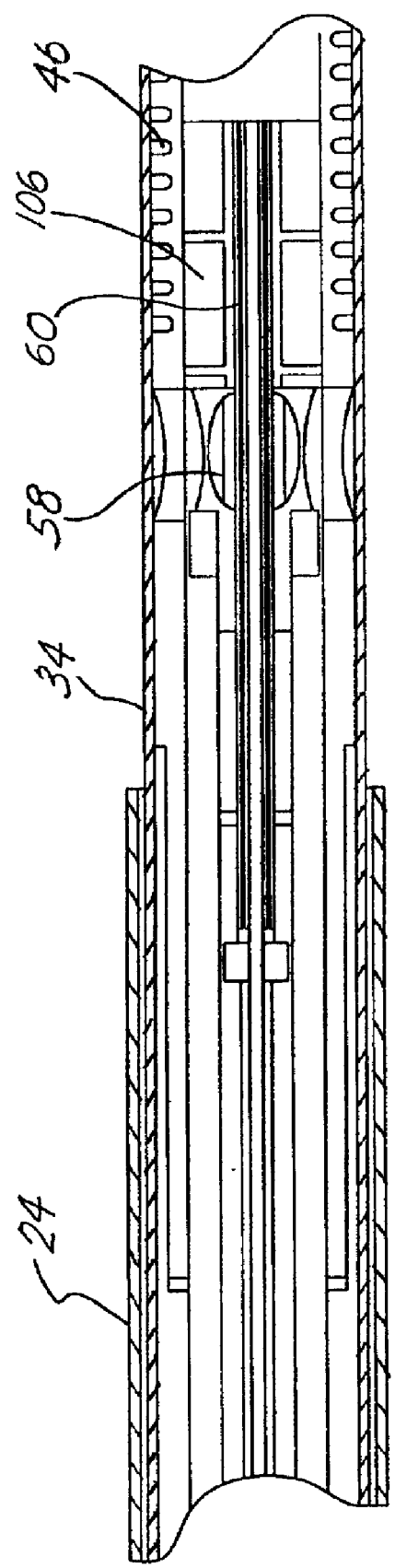
FIG. 4 is an enlarged view of the view shown in FIG. 3.

FIG. 1 shows a medical device 10 having a handgrip portion 12 and a thermal ablation catheter 14 removably connected thereto. Various cables are provided for connecting the medical device 10 to external sources. For example, a fluid line 16 is provided for connecting the medical device 10 to a fluid source (not shown). Further, a cable 18 is provided for connecting the medical device 10 to a controller (not shown). A pressure cable 20 is provided for monitoring pressure throughout the procedure. In addition, an impeller cable 22 is also provided for reasons discussed hereinafter.

Figure 6:
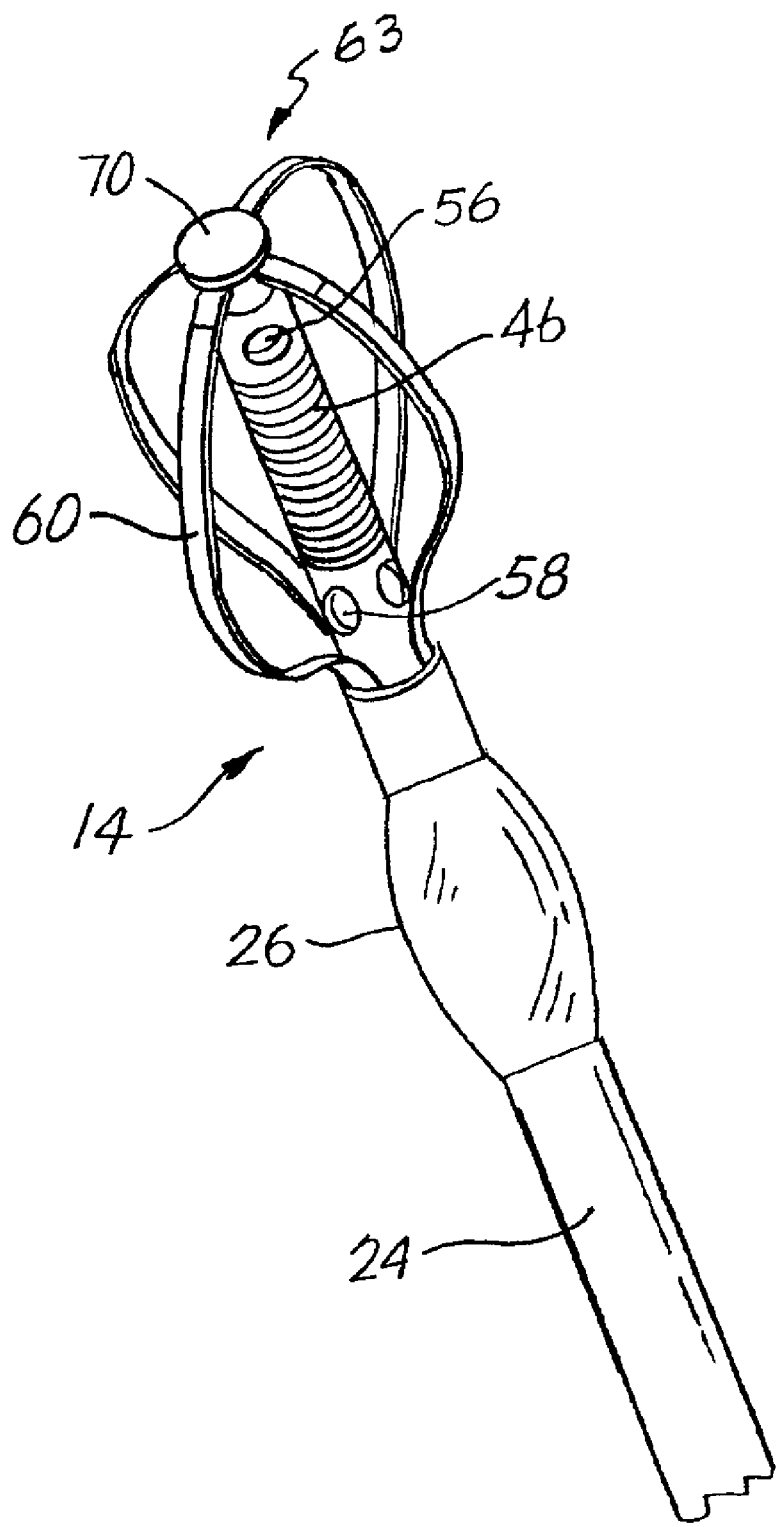
FIG. 6 is a perspective view of the thermal ablation catheter shown in FIG. 2, which shows the deployable cage assembly in a deployed configuration and the distensible bladder in an expanded configuration.

With reference to FIG. 2, the thermal ablation catheter 14 includes an outer sheath or tubular member 24 and a distensible bladder 26 attached thereto. For reasons to be discussed hereinafter, the distensible bladder 26 is sized and shaped to inflate into a fully expanded configuration as shown in FIG. 6 and to deflate into a fully collapsed configuration as shown in FIG. 2. Referring to FIG. 1, a passageway (not shown) is provided for receiving air and vacuum and is connected to an exterior line 28.

With reference to FIG. 2, the passageway is connected to a perforation in the form of a vent 29, which is formed on the tubular member 24, located underneath the distensible bladder 26. The air supplied via the passageway can be used to inflate the distensible bladder 26 to its fully expanded configuration as shown in FIG. 6, and the vacuum supplied via the passageway can be used to deflate the distensible bladder 26 to its fully collapsed configuration as shown in FIG. 2.

As illustrated in FIG. 2, the tubular member 24 includes a proximal end 30 which is sized and shaped to be insertable into the handgrip portion 12 (see FIG. 1) and a distal end 32 which is sized and shaped to be insertable into the uterus for reasons discussed hereinafter. The tubular member 24 is made from a material, such as stainless steel, teflon, or silicone, which can have a range of stiffness from rigid to flexible. The tubular member 24 has a length of approximately 230 mm and a diameter in a range from about 3 mm to about 10 mm. It will be understood that the above dimensions for the tubular member 24 are merely exemplary and that the tubular member 24 can have other dimensions. The distensible bladder 26 is made from a material, such as latex, silicone, or other elastomeric material, and when inflated, conforms to the shape of the cervical canal so as to seal the cervical canal, as will be discussed in greater detail hereinafter.

Figure 5:
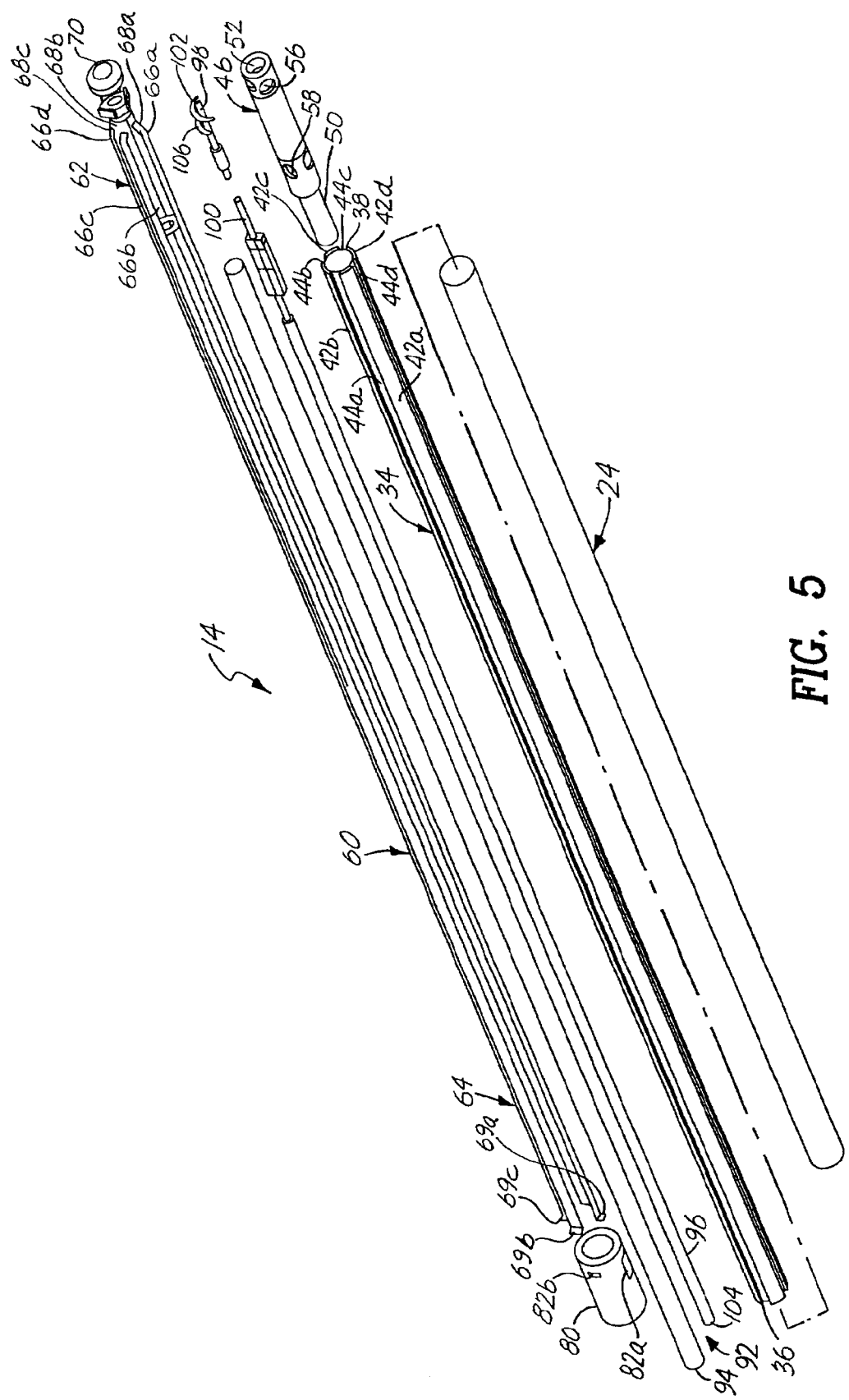
FIG. 5 is an exploded, perspective view of the thermal ablation catheter shown in FIG. 2, illustrated without the distensible bladder.

Referring to FIG. 5, the thermal ablation catheter 14 further includes a fluid stem 34 sized and shaped to be coaxially received within the tubular member 24. The fluid stem 34 includes a proximal end 36 and a distal end 38. A passageway (not shown) is provided for receiving a fluid (e.g., water, saline solution, high viscous gelatins, glycerol, propylene glycol, etc.). Although any of the fluids can be used, the preferred fluids are the high viscous gelatins due to their controllability. The passageway extends between the proximal end 36 and the distal end 38 and is connected to the fluid line 16 (see FIG. 1).

Still referring to FIG. 5, the fluid stem 34 has four longitudinal grooves on its outer surface so as to form four longitudinally extending bars 42a–d. A longitudinal groove 44a is formed between an adjacent pair of bars 42a–b, while a longitudinal groove 44b is formed between an adjacent pair of bars 42b–c. Also, a longitudinal groove 44c is formed between an adjacent pair of bars 42c–d, while a longitudinal groove 44d is formed between an adjacent pair of bars 42d–a.

The fluid stem 34 is made from a material, such as stainless steel, Teflon, nitinol, etc. As illustrated in FIG. 5, the fluid stem 34 has a diameter that is smaller than that of the tubular member 24.

With reference to FIG. 5, a heating assembly 46 is provided and is sized and shaped to be coaxially received within the fluid stem 34. More particularly, the heating assembly 46 has a heater core 52 which extends from the tubular member 24, when assembled as shown in FIG. 2, and an extension 50 which is sized and shaped to be coaxially received within the distal end 38 of the fluid stem 34. Referring to FIGS. 7 and 8, the heating assembly 46 includes a heater filament or wire 54 wrapped around the heater core 52. Heater wire leads (not shown) extend between the cable 18 (see FIG. 1) and the heating wire 54. A plurality of fluid outlet ports 56 is circumferentially positioned adjacent a distal end 57 of the heating assembly 46, while a plurality of fluid inlet ports 58 is circumferentially positioned adjacent a proximal end 59 of the heating assembly 46. The fluid outlet ports 56 and the fluid inlet ports 58 are in communication with the passageway of the fluid stem 34 (see FIG. 5). Thermocouples 61 can be employed within the heating assembly 46 to provide monitoring and control of the temperature within the uterine cavity 118.

FIG. 5 illustrates a deployable cage assembly 60 which cooperates with the fluid stem 34 and is coaxially received over the heating assembly 46. The deployable cage assembly 60 is sized and shaped to move between a deployed configuration as shown in FIG. 6, and a relaxed configuration as shown in FIG. 2. Referring to FIG. 5, the deployable cage assembly 60 has a distal portion 62 which is coaxially received over the heating assembly 46 and a proximal portion 64 which cooperates with the fluid stem 34.

Still referring to FIG. 5, the deployable cage assembly 60 includes four longitudinally extending arms 66a–d, each of which is movable from a relaxed configuration (see FIG. 2), in which the extending arms 66a–d are proximate to the thermal ablation catheter 14 and have an unbowed shape, to a deployed configuration (see FIG. 6), in which the extending arms 66a–d have a bowed shape and cooperate with each other to form an arcuate-shaped open structure 63 (see FIG. 6), which extends radially outward from the thermal ablation catheter 14. The open structure 63 is located on the distal portion 62 of the deployable cage assembly 60 and is exposed (i.e., not covered by the tubular member 24). More particularly, the extending arm 66a is sized and shaped to be received within the longitudinal groove 44a formed between the bars 42a–b of the fluid stem 34, while the extending arm 66b is sized and shaped to be received within the longitudinal groove 44b formed between the bars 42b–c of the fluid stem 34. Also, the extending arm 66c is sized and shaped to be received within the longitudinal groove 44c formed between the bars 42c–d, while the extending arm 66d is sized and shaped to be received within the longitudinal groove 44d formed between the bars 42d–a. The extending arm 66a has a fixed end 68a at the distal portion 62 and a tab 69a at a free end and at the proximal portion 64 extending perpendicularly to the extending arm 66a, while the extending arm 66b has a fixed end 68b at the distal portion 62 and a tab 69b at a free end and at the proximal portion 64 extending perpendicularly to the extending arm 66b. Further, the extending arm 66c has a fixed end 68c at the distal portion 62 and a tab 69c at a free end and at the proximal portion 64 extending perpendicularly to the extending arm 66c, while the extending arm 66d has a fixed end (not shown) at the distal portion 62 and a tab (not shown) at a free end and at the proximal portion 64 extending perpendicularly to the extending arm 66d.

Figure 9:
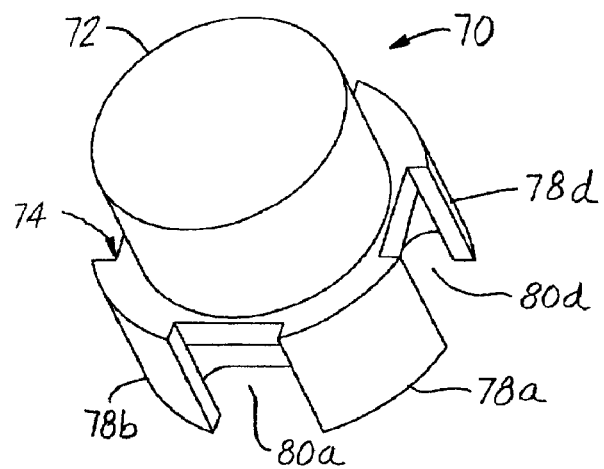
FIG. 9 is a top perspective view of a cap.
Figure 10:
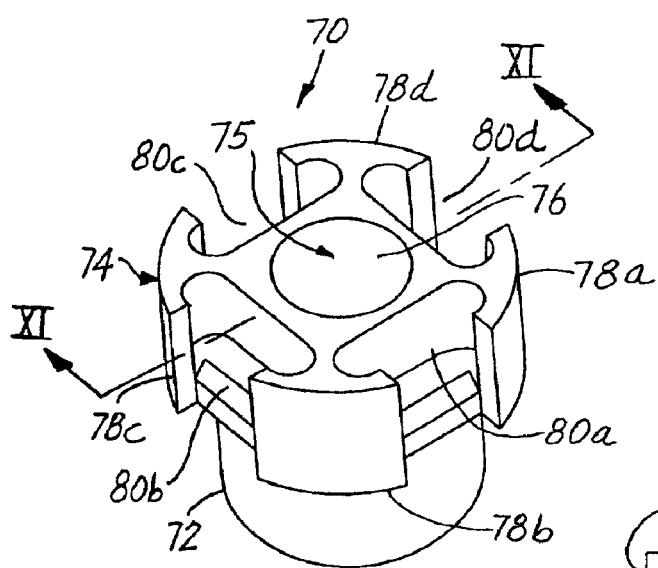
FIG. 10 is a bottom perspective view of the cap shown in FIG. 9.
Figure 11:
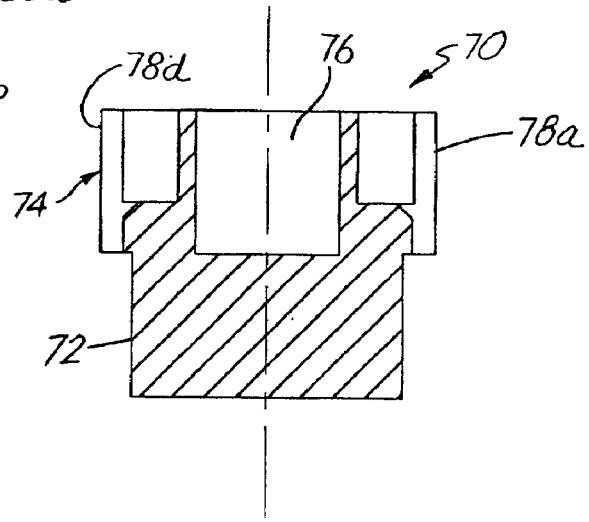
FIG. 11 is a cross-sectional view of the cap shown in FIG. 10, taken along section lines XI—XI and looking in the direction of the arrows.

With reference to FIG. 5, a cap 70 is connected to the extending arms 66a–d at the distal portion 62 of the deployable cage assembly 60 and is coaxially received over the distal end 57 of the heating assembly 46 (see FIG. 7). Referring to FIGS. 9–11, the cap 70 includes a cylindrical portion 72 and a connecting element 74 attached thereto. The connecting element 74 includes a center portion 75 defined by a lumen 76 sized and shaped to coaxially receive the distal end 57 of the heating assembly 46 (see FIG. 7), and also includes four projections 78a–d extending from the center portion 75. An opening 80a is formed between an adjacent pair of projections 78a–b and is sized and shaped to receive the end 68a of the extending arm 66a (see FIG. 5), while an opening 80b is formed between an adjacent pair of projections 78b–c and is sized and shaped to receive the end 68b of the extending arm 66b (see FIG. 5). Also, an opening 80c is formed between an adjacent pair of projections 78c–d and is sized and shaped to receive the end 68c of the extending arm 66c (see FIG. 5), while an opening 80d is formed between an adjacent pair of projections 78d–a and is sized and shaped to receive the end of the extending arm 66d (see FIG. 5).

With reference to FIG. 5, the deployable cage assembly 60 also includes a mating element 80 located at the proximal portion 64 and sized and shaped to be received within the handgrip portion 12 (see FIG. 1). As will be discussed in greater detail hereinafter, the mating element 80 is movable between a retracted position, in which the tabs 69a–c of the extending arms 66a–d are spaced a first distance from the fix ends 68a–c thereof, and an extended position, in which the tabs 69a–c are spaced a second distance from the fixed ends 68a–c, the second distance being less than the first distance. The mating element 80 has a plurality of circumferentially spaced slots. More particularly, a slot 82a is sized and shaped to mate with the tab 68a of the extending arm 66a, while a slot 82b is sized and shaped to mate with the tab 68b of the extending arm 66b. Also, a slot (not shown) is sized and shaped to mate with the tab 68c of the extending arm 66c, while a slot (not shown) is sized and shaped to mate with the tab of the extending arm 66d.

Figure 12:
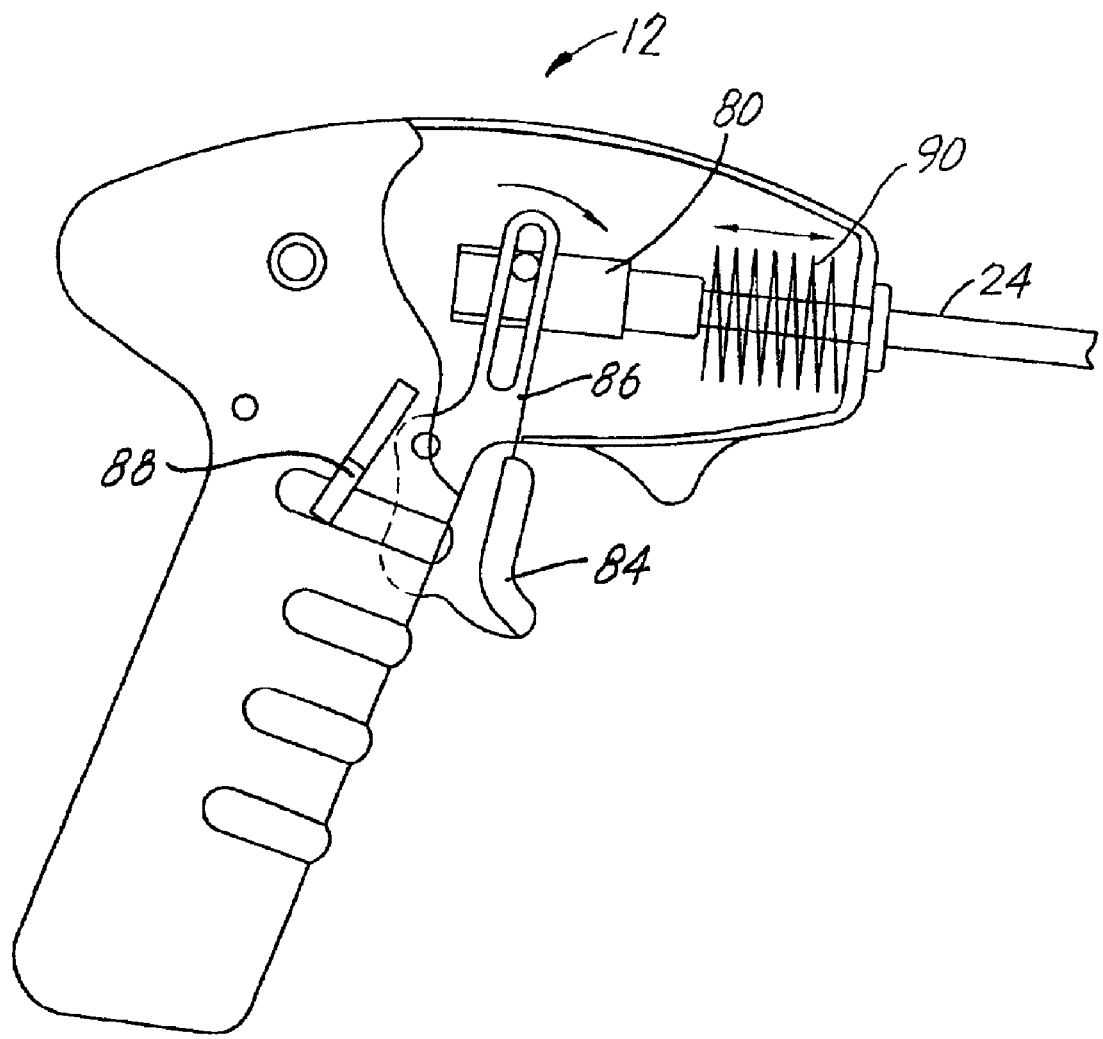
FIG. 12 is a partial, cross-sectional view of a handgrip portion shown in FIG. 1.

As illustrated in FIG. 12, the handgrip portion 12 has a finger trigger 84 and an actuating arm 86 attached thereto, such that when the finger trigger 84 is depressed, the actuating arm 86 slides the mating element 80 in a direction toward the cap 70 (see FIG. 2). As the actuating arm 86 slides the mating element 80 toward the cap 70, the extending arms 66a–d of the distal portion 62 (see FIG. 5) of the deployable cage assembly 60 move so as to place the deployable cage assembly 60 into its deployed configuration as shown in FIG. 6. A lock 88 is provided to maintain the deployable cage assembly 60 into its deployed configuration. When the lock 88 and the finger trigger 84 are released, a spring 90 urges the mating element 80 in a direction away from the cap 70 (see FIG. 2). As the spring 90 urges the mating element 80 away from the cap 70, the extending arms 66a–d of the distal portion 62 (see FIG. 5) of the deployable cage assembly 60 move so as to place the deployable cage assembly 60 into its relaxed configuration as shown in FIG. 2.

The extending arms 66a–d are made from a material, such as spring steel, stainless steel, etc. More particularly, the deployable cage assembly 60 has a length in a range of from about 30 mm to about 80 mm and a diameter in a range from about 3 mm to about 10 mm, when undeployed, and a diameter of about 20 mm to 40 mm when deployed. It will be understood that the above dimensions for the deployable cage assembly 60 are merely exemplary and that the deployable cage assembly 60 can have other dimensions.

Referring to FIG. 5, the medical device 10 further includes an impeller cable assembly 92 having an outer tube 94 and an inner tube 96 retained within the outer tube 94. The impeller cable assembly 92 includes a rotary impeller 98 for circulating fluid for reasons described hereinafter and a rotary drive cable 100 for driving the rotary impeller 98. More particularly, the rotary drive cable 100 has a distal end 102 which is secured within the core 52 of the heating assembly 46 and a proximal end 104 which is connected to the impeller cable 22 (see FIG. 1). As illustrated in FIG. 5, the rotary impeller 98 includes a plurality of blades 106 attached to the rotary drive cable 100. The blades 106 can be made from a metal or non-metal material. The impeller cable assembly 92 and the heater core 52 of the heating assembly 46 form a pump assembly.

Figure 14:
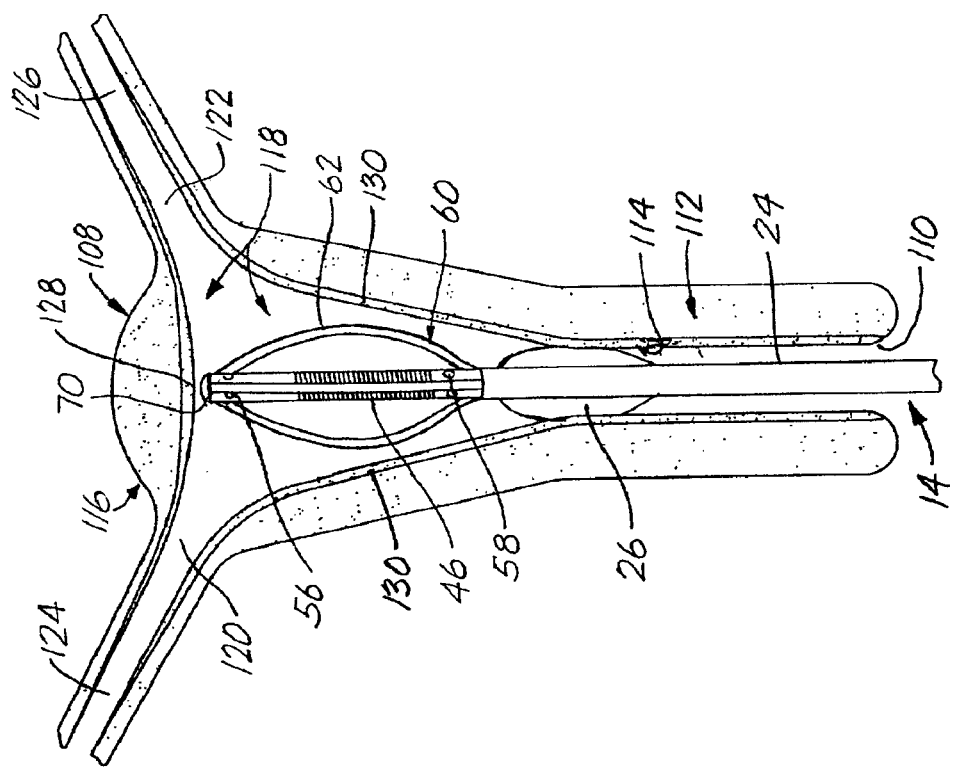
FIG. 14 is a view similar to the view shown in FIG. 13, except that the deployable cage assembly is in a deployed configuration and the distensible bladder is in an expanded configuration.
Figure 13:
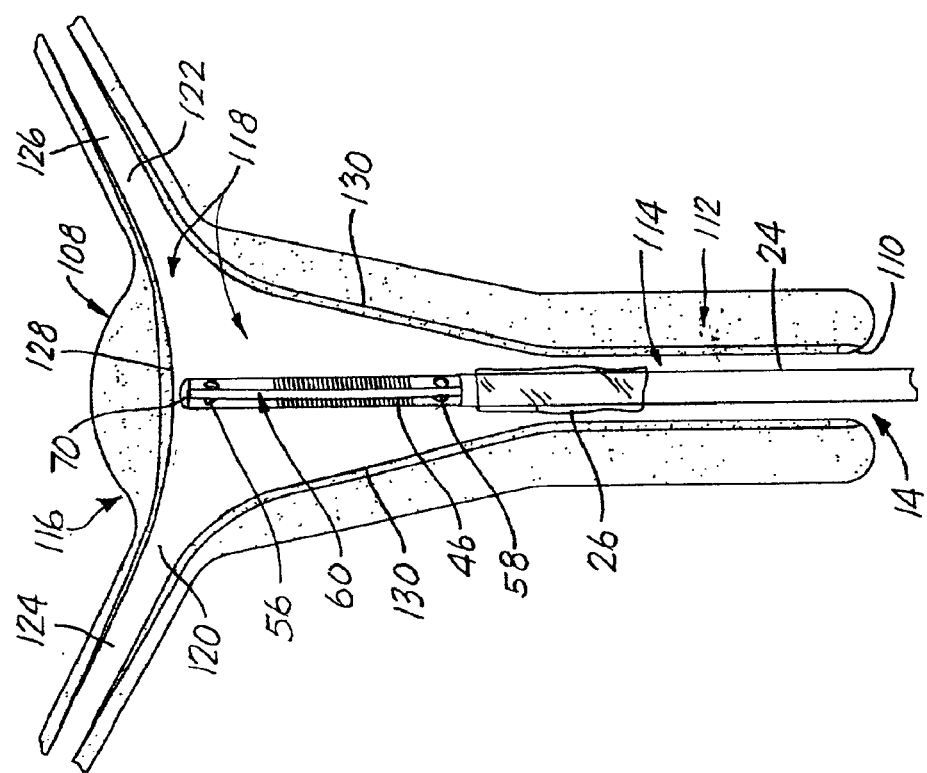
FIG. 13 is a schematic view of a female uterus and the thermal ablation catheter shown in FIG. 2, which shows a distal portion of the thermal ablation catheter in contact with the uterine cavity.

In order to fully understand the advantages of the medical device 10, a brief overview of the female uterus 108 is discussed below with reference to FIGS. 13–14. The female uterus 108 includes an external cervical opening 110; a cervix 112 having a cervical canal 114; an uterus 116 having an uterine cavity 118; tubal ostia 120, 122; and Fallopian tubes 124, 126. The uterine cavity 118 is joined to the Fallopian tubes 124, 126 via their respective tubal ostia 120, 122. As illustrated in FIGS. 13–14, the uterine cavity 118 includes a plurality of cavity walls in the form of a top wall (hereinafter referred to as a fundus 128) and side walls 130.

In operation, prior to inserting the thermal ablation catheter 14, the uterine sound (depth) is measured. More particularly, a sound (not shown) is inserted into the vaginal orifice (not shown) and guided through the cervical canal 114, and into the uterine cavity 118 until the sound is in contact with the fundus 128. The thermal ablation catheter 14 is then inserted into the vaginal orifice (not shown) until a distal portion of the thermal ablation catheter 14 enters the cervix 112. Note that in the foregoing step, the deployable cage assembly 60 is in its fully relaxed configuration and the distensible bladder 26 is in its fully collapsed configuration.

As illustrated in FIG. 13, the thermal ablation catheter 14 is then guided through the cervical canal 114, and into the uterine cavity 118 such that the cap 70 is in contact with the fundus 128 of the uterine cavity 118. In this position, the distal portion 62 of the deployable cage assembly 60 and the heating assembly 46 are positioned within the uterine cavity 118, while the distensible bladder 26 is positioned within the cervical canal 114. Turning now to FIG. 14, the distensible bladder 26 is then fully inflated with air, via the exterior line 28 (see FIG. 1) so as to assume its fully expanded configuration. When inflated, the distensible bladder 26 is in direct contact with the cervical canal 114 so as to serve as an endocervical seal and so as to thermally insulate the cervix 112 and the vaginal orifice (not shown). Next, the deployable cage assembly 60 is deployed, in the manner described previously, into its fully deployed configuration. When deployed, the cage assembly 60 serves to widen the uterine cavity 118 and to center the thermal ablation catheter 14 in place within the uterine cavity 118. Because the uterine cavity 118 has been widened, the deployable cage assembly 60 also serves to prevent direct contact between the heating assembly 46 and the tissues within the uterine cavity 118.

After the deployable cage assembly 60 in its fully deployed configuration and the distensible bladder 26 in its fully expanded configuration, fluid is supplied, via the fluid stem 34 and the fluid outlet ports 56, to the uterine cavity 118 at a predetermined pressure, until the uterine cavity 118 is filled with fluid. Alternatively, fluid can be injected into the uterine cavity 118 prior to deploying the cage assembly 60. When the fluid has filled the uterine cavity 118, the rotary drive cable 100 (see FIG. 5) is rotated so as to rotate the rotary impeller 98 (see FIG. 5), which causes the blades 106 (see FIG. 5) to agitate the fluid inside the uterine cavity 118. As the blades 106 rotate, the fluid is then conductively heated by the heating assembly 46 to a desired temperature, which is maintained for a predetermined time interval. It will be understood that the rotation of the blades 106 continues throughout the heating process. The rotary impeller 98 serves to provide uniform heating of the fluid by agitating the fluid surrounding the heating assembly 46. Because the fluid outlet ports 56 are positioned proximal to the fundus 128, the heated fluid initially dispenses against the fundus 128 and flows toward the cervical canal 114. Fluid is circulated within the uterine cavity 118 by flowing into the fluid inlet ports 58 and out of the fluid outlet ports 56, and the heated fluid thermally ablates the endometrial lining of the uterus 116. After a predetermined time interval, the power to the heating assembly 46 is terminated and the fluid is allowed to cool. The blades 106 continue to rotate until the fluid has reached a temperature at which it can be safely removed from the uterine cavity 118. Then, the cage assembly 60 is undeployed into its relaxed configuration. Next, the cooled fluid is removed, via all fluid ports 56, 58 and the fluid passageway (not shown), from the uterine cavity 118.

Thereafter, the distensible bladder 26 is deflated to its collapsed configuration. Lastly, the thermal ablation catheter 14 is removed from the uterine cavity 118, the cervical canal 114, and the vaginal orifice (not shown).

It should be appreciated that the present invention provides numerous advantages. For instance, the present invention enables the use of thermal ablation therapy for treating menorrhagia in women who have benign uterine pathology without employing a balloon in the uterine cavity 118. Because the distensible bladder 26 serves as an endocervical seal, the fluid is prevented from exiting the cervical canal 114 and the vaginal orifice. In such circumstances, only a small amount of fluid is required and the rotary impeller 98 can be small in size. Further, since the heating assembly 46 is used internally within the uterine cavity 118 and a small amount of fluid is required, a small amount of thermal energy is required. In addition, the thermocouples 61 actively monitor and control the temperature inside the uterine cavity 118.

It should be noted that the medical device 10 can have numerous modifications and variations. For instance, the thermal ablation catheter 14 can be either non-disposable or disposable. The rotary impeller 98 can be any fluid mixing element (e.g., pump) that serves to circulate fluid. Fluid (e.g., water or a saline solution) rather than air can be used to inflate the distensible bladder 26 to its fully expanded configuration. Various components of the thermal ablation catheter 14 can be integrally formed from a single tube. For instance, the outer tube 94 and the inner tube 96 of the impeller cage assembly 92 can be formed from a single tube. Also, various configurations of the fluid ports 56, 58 can provide fluid inlet and fluid outlet from any or all of the fluid ports 56, 58. The medical device 10 may also employ separate passageways for receiving air and vacuum, rather than a single passageway. Further, the ablation catheter 14 may employ alternative energy sources such as RF (radio frequency), laser, ultrasound, chemical, and/or a cryogenic device. All such variations and modifications are intended to be included within the scope of the invention as defined in the appended claims.

What is claimed is:

1. A method for performing thermal ablation therapy using a medical device which includes a thermal ablation catheter and a deployable cage assembly attached to a distal end of said thermal ablation catheter, said method comprising the steps of:

(a) inserting said distal end of said thermal ablation catheter into a cavity so as to insert said deployable cage assembly into the cavity and so as to insert a distensible bladder into the cervical canal, wherein said deployable cage assembly is inserted into the cavity and said distensible bladder is inserted into the cervical canal at the same time;

(b) deploying said cage assembly such that said deployable cage assembly forms an open structure which extends outward from said thermal ablation catheter;

(c) supplying a fluid to the cavity through said thermal ablation catheter;

(d) conductively heating the fluid within the cavity to a desired temperature and maintaining the temperature for a desired time period;

(e) providing said distensible bladder on said thermal ablation catheter; and (f) inflating said distensible bladder when said distensible bladder is positioned within the cervical canal and prior to the performance of step (d).

2. The method of claim 1, further comprising the step of:

(g) agitating the fluid within the cavity as the fluid is being conductively heated.

3. The method of claim 2, further comprising the step of:

(h) circulating the fluid within the cavity.

4. The method of claim 3, further comprising the step of:

(i) monitoring and controlling the temperature of the fluid within the cavity.

5. The method of claim 1, wherein step (f) includes supplying air to said distensible bladder so as to inflate said distensible bladder.

6. The method of claim 1, wherein said medical device includes a handgrip portion having a finger trigger and said thermal ablation catheter includes a slidable element cooperating with said finger trigger such that said slidable element moves in a direction toward said distal end of said thermal ablation catheter when said finger trigger is depressed.

7. The method of claim 6, wherein step (b) includes depressing said finger trigger of said handgrip portion such that said slidable element moves in a direction toward said distal end of said thermal ablation catheter so as to deploy said cage assembly.

8. The method of claim 1, wherein said thermal ablation catheter includes a fluid stem with a fluid inlet port and a fluid outlet port.

9. The method of claim 8, wherein step (c) includes supplying the fluid to the cavity via said fluid stem and said fluid outlet port.

10. The method of claim 8, further comprising the step of:

(g) circulating the fluid within the cavity by flowing the fluid through said fluid outlet port and through said fluid inlet port.

11. The method of claim 8, wherein said thermal ablation catheter includes a heating assembly positioned between said fluid inlet port and said fluid outlet port of said fluid stem.

12. The method of claim 11, wherein step (d) includes activating said heating assembly so as to conductively heat the fluid.

13. The method of claim 11, wherein said heating assembly includes thermocouples.

14. The method of claim 13, further comprising the step of:

(g) providing said thermocouples so as to monitor and control the temperature of the fluid within the cavity.

* * * * *